(12) United States Patent
Roberts et al.

(10) Patent No.: US 9,632,095 B2
(45) Date of Patent: Apr. 25, 2017

(54) DEVICE AND METHOD FOR DETERMINING REACTION KINETICS

(71) Applicant: UNIVERSITY OF DELAWARE, Newark, DE (US)

(72) Inventors: Christopher J. Roberts, West Grove, PA (US); Gregory V. Barnett, Plainsboro, NJ (US); Vladimir I. Razinkov, Thousand Oaks, CA (US); Bruce A. Kerwin, Bainbridge Island, WA (US)

(73) Assignees: UNIVERSITY OF DELAWARE, Newark, DE (US); AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/942,117

(22) Filed: Nov. 16, 2015

(65) Prior Publication Data
US 2016/0154004 A1 Jun. 2, 2016

Related U.S. Application Data

(60) Provisional application No. 62/085,837, filed on Dec. 1, 2014.

(51) Int. Cl.
*G01N 33/00* (2006.01)
*G01N 25/20* (2006.01)
(Continued)

(52) U.S. Cl.
CPC ......... *G01N 33/6845* (2013.01); *G01N 33/50* (2013.01)

(58) Field of Classification Search
CPC ........ G01N 33/00; G01N 25/20; G01N 25/00; G01N 31/00; G01N 33/48; G01N 33/50
(Continued)

(56) References Cited

U.S. PATENT DOCUMENTS 6,453,241 B1 * 9/2002 Bassett et al. ............... 702/19
6,618,144 B1 9/2003 Reed
(Continued)

OTHER PUBLICATIONS

Alb, A.M. et al., "In Situ time-dependent signatures of light scattered from solutions undergoing polymerization reactions," Feb. 24, 2004, pp. 2578-2587. vol. 37(7), Macromolecules.
(Continued)

*Primary Examiner* — Brian J Sines
(74) *Attorney, Agent, or Firm* — RatnerPrestia

(57) ABSTRACT

A method of determining the activation energy $E_a$ for degradation of a chemical species includes in sequence the steps of a) simultaneously incubating a plurality of samples of the chemical species in a single unitary device at a plurality of constant temperatures T, in each case for an incubation time t selected to result in loss of at most 20 mol % of the amount originally present; b) quenching each of the samples to stop degradation; c) determining the mole fraction m of the chemical species remaining in each of the quenched samples, relative to the amount present before incubating; d) determining for each sample a reaction rate coefficient $k_{obs}$ according to the equation $$k_{obs}(T) = \frac{1-m(T)}{t};$$

and e) performing numerical regression of the $k_{obs}$ values obtained in step d) and the corresponding temperatures T in ° K to derive the activation energy $E_a$ according to the following equation $$k_{obs} = k_0 \exp\left(\frac{E_a}{R}\left(\frac{1}{T} - \frac{1}{T_0}\right)\right),$$

(Continued)

or to derive a temperature-dependent activation energy if that is more appropriate for the chemical species of interest.

14 Claims, 6 Drawing Sheets

(51) Int. Cl.
| | |
|---|---|
| G01N 25/00 | (2006.01) |
| G01N 31/00 | (2006.01) |
| G01N 33/48 | (2006.01) |
| G01N 33/50 | (2006.01) |
| G01N 33/68 | (2006.01) |

(58) Field of Classification Search
USPC .... 422/68.1, 82.12; 436/34, 43, 86, 87, 147; 702/22, 23, 19, 30, 130, 136
See application file for complete search history.

(56) References Cited

U.S. PATENT DOCUMENTS

| | | | |
|---|---|---|---|
| 7,033,840 B1* | 4/2006 | Tagge et al. | 436/147 |
| 7,075,652 B1* | 7/2006 | Sarvazyan et al. | 356/432 |
| 2012/0107904 A1* | 5/2012 | Fox et al. | 435/189 |

OTHER PUBLICATIONS

Carpenter, J.F., et al.; "Overlooking subvisible particles in therapeutic protein products: Gaps that may compromise product quality," Apr. 2009, pp. 1201-1205, vol. 98(4), Journal of Pharmaceutical Sciences.
Drenski, M. F., et al., "Monitoring protein aggregation kinetics with simultaneous multiple sample light scattering," 2013, pp. 185-197, vol. 437, Analytical Biochemistry.
Drenski, M.F., et al.. "Simultaneous in-situ monitoring of parallel polymerization reactions using fight scattering; a new tool for high-throughput screening," Jul. 16, 2004; pp. 710-716, vol. 6(5), J. Combinatorial Chemistry.
Drenski, M.F., et al,, "Simultaneous multiple sample light scattering for analysis of polymer solutions," 2004, pp. 2724-2732, vol. 92, Journal of Applied Polymer Science.
Hartl, F.U., et al,, "Converging concepts of protein folding in vitro and in vivo," Jun. 2009, pp. 574-581. vol. 16(6), Nature Structural & Molecular Biology.
Latypov, R.F. at al., "Elucidation of acid-induced unfolding and aggregation of human immunogiobulin IgG1 and IgG2 Fc," Jan. 6, 2012, pp. 1331-1396, vol. 287(2), The Journal of Biological Chemistry.
Multi-Temperature Zone Reaction Blocks, downloaded Aug. 12, 2015 from www.jkem.com.
Pace, A.L. et al., "Asparagine deamidation dependence on buffer type, pH, and temperature," Jun. 2013, pp. 1712-1723, vol. 102(6), Journal of Pharmaceutical Sciences.
Rosenberg, A.S., et al., "Effects of protein aggregates: An immunologic perspective," Aug. 4, 2006, pp. E501-E507, vol. 8(3), Article 59, The AAPS Journal 2006.
Vlasak, J., et al., "Fragmentation of monoclonal antibodies," May 1, 2011, mAbs, 3:3, pp. 253-263.
Wang, W., et al., "Imrnunogenicity of protein aggregates-concerns and realities," Apr. 21, 2012, pp. 1-11, vol. 431, International Journal of Pharmaceutics.
Wang, W., et al,, "Non-Arrhenius protein aggregation," Jul. 2013, pp. 840-851, vol. 15(3), The AAPS Journal.
Wu, H. et al.. "Competing aggregation pathways for monoclonal antibodies," Feb. 12, 2014, pp. 936-941, FEBS Letters 588.
Brummitt et al., Nonnative Aggregation of an IgG1 antibody in acidic conditions: Parat 1. Unfolding colloidal interactions, and formation of high-molecular-weight aggegates, J. Pharm. Sci. 100 (2011) pp. 2087-2103.
Brummitt, et al., Nonnative Aggregation of an IgGl Antibody in Acidic Conditions. Part 2: Nucleation and Growth Kinetics with Competing Growth Mechanisms, J. Pharm. Sci. 2011, 100, pp. 2014-2119.
Brummitt et al., "Predicting Accelerated Aggregation Rates for Monoclonal Antibody Formulations, and Challenges for Low-Temperature Predictions", J. Pharm. Sci, 2011, 100, pp. 4234-4243.
Kim et al., Aggregation of anti-streptavidin immunoglobulin gamma-1 involves Fab unfolding and competing growth pathways mediated by pH and salt concentration, Biophys. Chem 172 (2013), pp. 26-36.
C.J. Roberts, T.K. Das, E. Sahin, Predicting solution aggregation rates for therapeutic proteins: Approaches and challenges, Int. J. Pharm. 418 (2011) 18-333.
M. F. Drenski, W. F. Reed, "Simultaneous Multiple Sample Light Scattering (SMSLS)", Polymeric Materials: Science & Engineering 2003, 88, 304-305.
Weiss, W F.; Young, T. M.; Roberts, C. J. Principles, Approaches, and Challenges for Predicting Protein Aggregation Rates and Shelf Life, J. Pharm. Sci. 2009, 98, 1246-1277.
Andrews. J. M.; Roberts. C. J. A Lumry-Eyring Nucleated Polymerization Model of Protein Aggregation Kinetics: 1. Aggregation with Pre-Equilibrated Unfolding, J, Phys, Chem. B 2007, 111, 7897-7913.
Li, Y.; Roberts, C. J. Lumry-Eyring Nucleated-Polymerization Model of Protein Aggregation Kinetics. 2. Competing Growth via Condensation and Chain Polymerization. J. Phys. Chem. B 2009, 113, 7020-7032.
G. Walsh, Biopharmaceutical benchmarks 2014, Nat. Biotechnol. 32 (2014) 992-1000.
S.R. Aggarwal, What's fueling the biotech engine 2012 to 2013, Nature. 201 (2014) 4.
M. Vázquez-Rey, D.A. Lang, Aggregates in monoclonal antibody manufacturing processes, Biotechnol. Bioeng. 108 (2011) 1494-1508.
E. Sahin, W.F. Weiss, A.M. Kroetsch, K.R. King, R.K. Kessler, T.K. Das, et al., Aggregation and pH-temperature phase behavior for aggregates of an IgG2 antibody, J. Pharm. Sci. 101 (2012) 1678-1687.
C.J. Roberts, D.P. Nesta, N. Kim, Effects of Temperature and Osmolytes on Competing Degradation Routes for an IgG1 Antibody: Competing Degradation Routes for an IgG1 Antibody, J. Pharm. Sci. 102 (2013) 3556-3566.
C.J. Roberts, T.K. Das, E. Sahin, Predicting solution aggregation rates for therapeutic proteins: Approaches and challenges, Int. J. Pharm. 418 (2011) 318-333.
A. Hawe, M. Wiggenhorn, M. van de Weert, J.H.O. Garbe, H. Mahler, W. Jiskoot, Forced degradation of therapeutic proteins, J. Pharm. Sci. 101 (2012) 895-913.
N. Kim, R.L. Remmele, D. Liu, V.I. Razinkov, E.J. Fernandez, C.J. Roberts. Aggregation of anti-streptavidin immunoglobulin gamma 1 involves Fab unfolding and competing growth pathways mediated by pH and salt concentration, Biophys. Chem. 172 (2013) 26-36.
F. He, C.E. Woods, G.W. Becker, L.O. Narhi, V.I. Razinkov, High-throughput assessment of thermal and colloidal stability parameters for monoclonal antibody formulations, J. Pharm. Sci. 100 (2011) 5126-5141.
D.S. Goldberg, S.M. Bishop, A.U. Shah, H.A. Sathish, Formulation development of therapeutic monoclonal antibodies using high-throughput fluorescence and static light scattering techniques: Role of conformational and colloidal stability, J. Pharm. Sci. 100 (2011) 1306-1315.
W. Cheng, S.B. Joshi, F. He, D.N. Brems, B. He, B.A. Kerwin, et al., Comparison of high-throughput biophysical methods to identify stabilizing excipients for a model IgG2 monoclonal antibody: Conformational stability and kinetic aggregation measurements, J. Pharm. Sci. 101 (2012) 1701-1720.
A. Bhambhani, J.M. Kissmann, S.B. Joshi, D.B. Volkin, R.S. Kashi, C.R. Middaugh, Formulation design and high-throughput excipient selection based on structural integrity and conformational stability of dilute and highly concentrated IgG1 monoclonal antibody solutions, J. Pharm. Sci. 101 (2012) 1120-1135.

(56) References Cited

OTHER PUBLICATIONS

E. Ablinger, S. Leitgeb, A. Zimmer, Differential scanning fluorescence approach using a fluorescent molecular rotor to detect thermostability of proteins in surfactant-containing formulations, Int. J. Pharm. 441 (2013) 255-260.

T. Menzen, W. Friess, High-throughput melting-temperature analysis of a monoclonal antibody by differential scanning fluorimetry in the presence of surfactants, J. Pharm. Sci. 102 (2013) 415-428.

Y. Li, B.A. Ogunnaike, C.J. Roberts, Multi-variate approach to global protein aggregation behavior and kinetics: Effects of pH, NaCl, and temperature for a-chymotrypsinogen A, J. Pharm. Sci. 98 (2009) 3997-4016.

P. Arosio, S. Rima, M. Lattuada, M. Morbidelli, Population Balance Modeling of Antibodies Aggregation Kinetics, J. Phys. Chem. B, 116 (2012) 7066-7075.

L. Yi, N. Beckley, B. Gikanga, J. Zhang, Y.J. Wang, H.-W. Chih, et al., Isomerization of Asp-Asp motif in model peptides and a Monoclonal Antibody Fab Fragment, J. Pharm. Sci. 102 (2013) 947-959.

D.D. Banks, R.F. Latypov, R.R. Ketchem, J. Woodard, J.L. Scavezze, C.C. Siska, et al., Native-state solubility and transfer free energy as predictive tools for selecting excipients to include in protein formulation development studies, J. Pharm. Sci. 101 (2012) 2720-2732.

S.B. Hari, H. Lau, V.I. Razinkov. S. Chen, R.F. Latypov, Acid-Induced Aggregation of Human Monoclonal IgG1 and IgG2: Molecular Mechanism and the Effect of Solution Composition, Biochemistry. 49 (2010) 9328-9338.

B.D. Mason, C. Schöneich, B.A. Kerwin, Effect of pH and light on aggregation and conformation of an IgG1 mAb, Mol. Pharm. 9 (2012) 774-790.

R.M. Ionescu, J. Vlasak, C. Price, M. Kirchmeier, Contribution of variable domains to the stability of humanized IgG1 monoclonal antibodies, J. Pharm, Sci. 97 (2008) 1414-1426.

T. Wang, O.S. Kumru, L. Yi, Y.J. Wang, J. Zhang, J.H. Kim, et al., Effect of ionic strength and pH on the physical and chemical stability of a monoclonal antibody antigen-binding fragment, J. Pharm. Sci. 102 (2013) 2520-2537. doi:10.1002/jps.2364.5.

B. Li, E.M. Gorman, K.D. Moore, T. Williams, R.L. Schowen, E.M. Topp, et al., Effects of acidic N" +" 1 residues on asparagine deamidation rates in solution and in the solid state, J. Pharm. Sci. 94 (2005) 666-675.

G.V. Barnett, V. Razinkov, B.A. Kerwin, T.M. Laue, A. Woodka, P. Butler, et al., Specific-Ion Effects on the Aggregation Mechanisms and Protein-Protein Interactions tor Anti-Streptavidin Immunoglobulin Gamma-1, published Apr. 17, 2015.

C.J. Roberts, Kinetics of Irreversible Protein Aggregation: Analysis of Extended Lumry Eyring Models and Implications for Predicting Protein Shelf Life, J. Phys. Chem. B. 107 (2003) 1194-1207. doi:10.1021/jp026827s.

C.J. Roberts, R.T. Darrington, M.B. Whitley, Irreversible aggregation of recombinant bovine granulocyte-colony stimulating factor (bG-CSF) and implications for predicting protein shelf life, J. Pharm. Sci. 92 (2003) 1095-1111.

U.D. of Health; H.S.F.C. for Drug, others, Guidance for industry: patient-reported outcome measures: use in medical product development to support labeling claims: draft guidance, Health Qual. Life Outcomes. 4 (2006) 79.

\* cited by examiner

DEVICE AND METHOD FOR DETERMINING REACTION KINETICS

CROSS REFERENCE TO RELATED APPLICATIONS

This application claims priority benefit of U.S. Appln. No. 62/085,837, filed Dec. 1, 2014, the entirety of which is incorporated herein by reference for all purposes.

STATEMENT REGARDING FEDERALLY SPONSORED RESEARCH

This invention was made with government support under Grant Numbers CBET 0931173, awarded by NSF, and 70NANB12H239, awarded by NIST. The government may have certain rights in the invention.

BACKGROUND OF THE INVENTION

Protein-based pharmaceuticals are one of the fastest growing sectors of the pharmaceutical pipeline. Monoclonal antibodies (mAbs) are expected to be among the leading candidates for biologic drugs in the future, with over 30 currently FDA-approved therapeutic products on the market. This class of proteins has the potential to treat many diseases, including various forms of cancer, autoimmune diseases, and life-threatening infections. However, mAbs and other protein-based therapeutics have inherent stability problems that can be problematic during manufacturing and storage. During processing, proteins may experience chemical, thermal, or mechanical stresses that lead to losses by chemical or physical degradation. During storage, the stresses may be reduced but proteins remain inherently labile molecules that can degrade during extended storage periods needed for commercial products. One example of physical degradation is aggregation. This, in particular, has the potential to jeopardize patient safety and drug efficacy if product administration leads to unwanted patient immune responses.

While the amino acid sequence ultimately dictates the three-dimensional structure of proteins, the surrounding solution environment also influences the conformational stability and propensity for non-native aggregation, i.e., aggregation via non-native conformational states. Solution pH, salt type and concentration, and the identity and concentration of other excipients may alter the chemical potential of the folded and unfolded states. Upon heating or applying other stresses, protein monomers (i.e., single protein molecules) can lose higher-order structure and biological function. As the same molecular forces that drive protein folding also drive protein aggregation, aggregated states are often expected to be lower in free energy than the folded or unfolded monomeric states when one operates at practical protein concentrations for therapeutic products. While thermodynamics may favor aggregates being the lowest free energy state, kinetics typically dictate the timescales and concentrations of the final aggregated populations. As such, measurement and prediction of aggregation rates is a major focus of effort during drug product development.

Non-native aggregation requires some degree of conformational change, as this allows otherwise buried regions of adjacent proteins to "bind" with one another. Larger aggregates can form via monomers adding to existing aggregates, or aggregates may coalesce with each other. As aggregation is a multi-step process, many stages have the potential to be the rate-limiting step. When one operates at temperatures significantly below the midpoint unfolding temperature(s), the unfolding/folding stage(s) will be pre-equilibrated because they occur much more quickly than the rate-limiting step(s) for aggregation. As such, unfolding thermodynamics will dictate the effective concentration of "reactive" protein molecules that are available to participate in the aggregation process, and this often results in aggregation rates that are highly sensitive to sample storage temperatures.

A priori prediction of aggregation rates for a protein in a given formulation remains an outstanding challenge for a variety of fundamental and practical reasons. The solution pH, choice of buffer species, and addition of salt and other excipients may affect conformational stability and/or protein-protein interactions, while temperature changes can dramatically effect conformational stability. Prior work has indicated that conformational stability is a key factor affecting aggregation rates in solution, as the midpoint temperature of thermal unfolding from differential scanning calorimetry, or the onset temperature of aggregation from scanning techniques, is often at least qualitatively predictive of aggregation rates across different formulations. However, there can also be a competing effect between changes in conformational stability and protein-protein interactions as one changes solution conditions such as pH.

A number of temperature-scanning techniques have been developed to at least qualitatively or semi-quantitatively monitor aggregation, but an inherent issue with these techniques is thermal history. For example, in the process of scanning through lower temperatures, one creates aggregates that can act as "seeds" to accelerate aggregation at subsequent (higher) temperatures, resulting in overestimation of aggregation rates. It is difficult to predict whether/when such seeding will occur, as simple changes in the formulation pH and ionic strength can alter aggregation mechanisms and "seeding" effects.

A large majority of biophysical techniques traditionally used to rapidly monitor aggregation use an indirect measure of monomer loss rates, providing only surrogate measures of aggregation. A direct measurement of monomer concentration necessitates separation of monomer from aggregate species or measuring a monomer-specific marker. For example, in spectroscopic techniques such as circular dichroism, ThT dye-binding or intrinsic fluorescence, the spectra are ensemble averages. Because the spectra have contributions from monomer and aggregate species, the spectral changes may or may not correlate with monomer consumption.

Indirect measures of monomer loss rates may also have bias, based on the measurement technique. For example, aggregation rates monitored using scattering techniques have a bias towards larger sized particles. In addition, dynamic and static scattering techniques are also convoluted with protein-protein interactions when one considers higher protein concentrations. As such, the putatively reported molecular weight or other measures of aggregate size are not generally correct under those conditions. This can also be a problem under conditions where protein monomers have long-ranged repulsions with one another. In addition, changes in ionic strength or pH can alter aggregation mechanisms, and produce large and heterogeneous aggregate populations that provide much larger scattering intensities compared to smaller-sized aggregates at identical monomer loss rates. These challenges are compounded if fragmentation occurs, as is relatively common for mAbs and other proteins.

Controlling and predicting unwanted degradation, including non-native aggregation, is a long-standing challenge in the effort to develop protein-based products. Aggregation rates are typically sensitive to temperature, pH, and the addition of excipients. Therefore, quantitatively comparing rates across multiple possible formulations is a key challenge in product development.

SUMMARY OF THE INVENTION

In some aspects, the invention provides a method of determining the activation energy $E_a$ for degradation of a chemical species, including in sequence the steps of a) simultaneously incubating a plurality of samples of the chemical species in a single unitary device at a plurality of constant temperatures T, wherein the incubation of each of the plurality of samples is performed for an incubation time t selected to result in loss of a portion of the chemical species, the portion being at most 20 mol % of the amount originally present;

b) quenching each of the samples in a manner sufficient to stop degradation;

c) determining the mole fraction m of the chemical species remaining in each of the quenched samples, relative to the amount present before incubating;

d) determining for each sample a reaction rate coefficient $k_{obs}$ according to the equation $$k_{obs}(T) = \frac{1 - m(T)}{t};$$

and e) performing numerical regression of the $k_{obs}$ values obtained in step d) and the corresponding temperatures T in ° K to derive the activation energy $E_a$ according to the following equation $$k_{obs} = k_0 \exp\left(\frac{E_a}{R}\left(\frac{1}{T} - \frac{1}{T_0}\right)\right)$$

wherein $k_0$ is the value of $k_{obs}$ for $T_0$, which can be one of the plurality of temperatures in ° K, or an arbitrary reference temperature of interest for a particular example.

In some aspects, the invention provides a method of determining the reaction rate coefficient ($k_{obs}$) for the degradation of a chemical species at each of a plurality of constant temperatures, including in sequence the steps of a) simultaneously incubating a plurality of samples of the chemical species in a single unitary device at the plurality of constant temperatures T, wherein the incubation of each of the plurality of samples is performed for an incubation time t selected to result in loss of a portion of the chemical species, the portion being at most 20 mol % of the amount originally present;

b) quenching each of the samples in a manner sufficient to stop degradation;

c) determining the mole fraction m of the chemical species remaining in each of the quenched samples, relative to the amount present before incubating; and d) determining for each sample a reaction rate coefficient $k_{obs}$ according to the equation $$k_{obs}(T) = \frac{1 - m(T)}{t}.$$

DETAILED DESCRIPTION OF THE INVENTION

Figure 1:
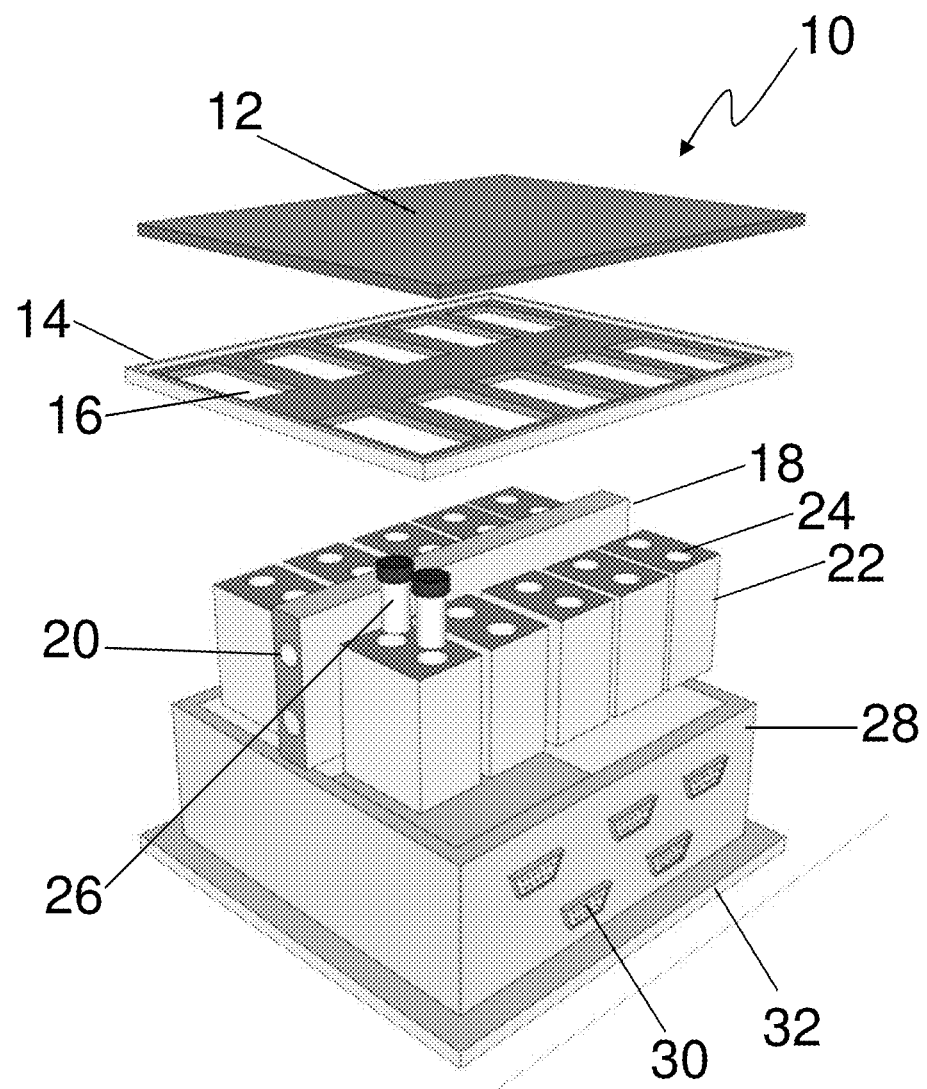
FIG. 1 is a schematic drawing of an exemplary device for performing the PTIR method according to the invention.

The inventors have now developed a Parallel-Temperature-Initial-Rates (PTIR) method that accurately and efficiently determines degradation rates as a function of temperature. An exemplary apparatus for doing this is also provided.

In conventional approaches, one determines monomer loss for multiple samples at a small number of temperatures (sometimes only one, e.g., 40° C.) over a predetermined incubation time (e.g., according to ICH guidelines). In the PTIR method of this invention, one instead determines monomer loss for a small number of samples (e.g., one sample in the extreme example below) at multiple temperatures for the same incubation time. That is, rather than take measurements at multiple incubation times at a given temperature, one takes measurements at multiple temperatures for a given incubation time. The incubation time is chosen to result in loss of at most 20 mol % of the protein monomer, or at most 10 mol %. The amount of monomer loss need only be enough to allow accurate and precise measurement. Typically, it will be at least 0.5 mol %, or at least 1, 2, or 4 mol %.

The aggregation rate for a given temperature from PTIR agrees with results from a traditional, isothermal method. However, PTIR has the advantage of providing activation energy ($E_a$) values that are either impractical to obtain with any reasonable certainty using traditional approaches, or are fundamentally of limited accuracy if one uses temperature-scanning methods. Within this context, it should be noted that $E_a$ values from experimental data necessarily have statistical uncertainty or confidence intervals (i.e., "error bars") because they require one to regress data versus a model such as the Arrhenius equation. Traditional isothermal methods require many samples at each temperature, and therefore have practical limits in that $E_a$ values are determined using a small number of temperatures. This necessarily leads to large uncertainties in $E_a$ values, making the data of limited use for setting product shelf lives or quantifying the stability of products as a function of temperature. The PTIR method provides accurate initial rate values for a given temperature, as well as activation energies having much better precision and reliability (i.e., small error bars) than those obtained by conventional approaches. For example, the error bars for the $E_a$ values from the data by the conventional approach in examples below are as large as the $E_a$ values themselves—this makes them statistically meaningless for prediction of sample stability at lower temperatures. In contrast, the PTIR based $E_a$ values have error bars that are much smaller and provide much more reliable interpolation and extrapolation of aggregation rates to other temperatures of interest. See Table 1 below. The PTIR method can easily be adapted for use with degradation routes other than non-native aggregation, and provides an efficient method to more accurately determine the temperature dependence of protein degradation rates, and potentially to predict long-term protein stability at much lower temperatures outside the range measured by a user with the PTIR method.

In some embodiments of the invention, the PTIR method provides rate coefficient (units of inverse time), $k_{obs}$, for protein aggregation processes, as well as activation energies $E_a$ for such processes. It also provides $k_{obs}$ and $E_a$ values for total degradation of proteins, i.e., losses due to aggregation and/or chemical degradation. For example, $k_{obs}$ and $E_a$ values for chemical degradation losses of proteins due to hydrolysis, for example deamidation, can be determined by this approach. More generally, these values can be determined for chemical species in general, for example drugs or pharmaceutical products of any type.

EXAMPLES

General Experimental Procedures

AS-IgG1 (>98% monomer) was provided by Amgen as a stock solution at a concentration of 30 mg/mL. Additionally, purified fragment crystallizable region (Fc-IgG1) was provided by Amgen as a stock solution at a concentration of 20 mg/ml. The protein was dialyzed as previously reported by Brummitt et al. *J. Pharm. Sci.* 100 (2011) 2087-2103 and by Kim et al., *Biophys. Chem.* 172 (2013) 26-36. The protein concentration was confirmed using UV-Vis absorbance at 280 nm (Agilent 8453 UV-Vis, Agilent Technologies, Santa Clara, Calif.) using an IgG1 extinction coefficient of 1.586 mL/mg cm and an Fc-IgG1 extinction coefficient of 1.36 mL/mg cm. All solutions were diluted gravimetrically to working concentrations.

Monomer concentrations were quantified using size exclusion chromatography (SEC). An Agilent 1100 HPLC (Agilent Technologies, Santa Clara, Calif.) was connected in-line to a Tosoh (Montgomeryville, Pa.) TSK-Gel 3000xL column. Samples were injected with an autosampler (100 microliter injections), with samples held at room temperature prior to injection. Concentration was determined by peak area, using a variable wavelength detector (Agilent technologies, Santa Clara, Calif.) and absorbance at 280 nm, with external standards. Additional details are the same as previously reported by Kim et al.

Differential scanning calorimetry (DSC) was performed using standard techniques as previously reported by Brummitt et al. and Kim et al.

Incubations were performed as follows. IgG1 stock solutions were prepared at 1 mg/mL at a given pH, NaCl concentration, and buffer type, and aliquotted into hermetically sealed deactivated borosilicate glass HPLC vials (Waters, Milford, Mass.). Isothermal incubations were performed by heating multiple samples at a given temperature in a water bath, or in the custom-built PTIR device shown schematically in FIG. 1, and removing samples at predetermined incubation times. Incubation temperatures were chosen such that samples could easily be removed at multiple points during the early periods of monomer loss, i.e., when m=1 to 0.8, where m is defined as the concentration of monomer divided by the initial monomer concentration, as measured by SEC peak area. At each time point, a given vial was immediately quenched by immersion in an ice-water bath to arrest aggregation, and was subsequently held at room temperature (20-23° C.) prior to analysis with SEC.

FIG. 1 is a schematic drawing of an exemplary device shown generally at 10, suitable for performing the PTIR method according to the invention. The device has a lid 12, an insulation plate 14 having placement windows 16 through which vials 26 can be placed into wells 24 in heating blocks 22, which are made of a thermally conductive metal, for example aluminum. The temperature of each of the heating blocks 22 is controlled independently by its own Peltier device (not shown), assisted by contact of the heating blocks 22 with a metal heat sink 18 whose temperature is maintained by flow of a heating or cooling liquid through passages 20. For ease of reference, the heating blocks 22 and the metal heat sink 18 are shown in FIG. 1 in a raised position relative to housing 28, but in practice they are enclosed within it. Housing 28 sits on base 32, and contains the Peltier devices and their electrical connections (not shown), which interface with one or more controller units (not shown) via electrical connectors 30.

In the particular embodiment shown in FIG. 1, the device has 10 independent Peltier-controlled metal heating blocks each capable of holding two 1.5 mL HPLC vials. The Peltier-controlled blocks are cooled with circulating water to maintain stable temperature control, and are insulated from each other and the surroundings.

In the present Examples, incubation temperatures were chosen so that samples quenched after 2 or 24 hours would have monomer loss values that fell in the initial-rate regime, i.e., at most 20 mol % loss of monomer. The incubation time was selected to be not less than 2 hours so as to allow for sufficient temperature equilibration and elimination of artificial lag times at shorter incubation time scales when samples were heating to the set-point temperature. Sample temperatures were confirmed independently with a separately calibrated thermocouple. The longer incubation timescale of 24 hours was chosen to achieve initial rates approximately one order of magnitude slower than 2 hours. For some examples, 10-day incubations were also performed.

Calculation of Aggregation Rates by PTIR Method

Aggregation rates were determined from the monomer fraction remaining as a function of incubation time, measured by SEC as described above. Over approximately the first ten to twenty percent monomer loss, the rate of change of m remains nearly constant and the observed rate law can therefore be well described as zeroth order without the need to assume an underlying rate law. Therefore, in the traditional method, for each temperature the monomer fraction was regressed with Equation [1] to obtain the aggregation rate coefficient (units of inverse time), $k_{obs}$, from the regime where m was between approximately 1 and 0.8, i.e., loss of at most 20 mol % of the protein monomer.

$$m = 1 - k_{obs} t \quad [1]$$

Aggregation rates, in units of 1/time, in the initial-rate regime are equivalent to rate coefficients, and are determined using the PTIR approach are based on Equation [2], which is derived by rearranging Eq. 1 and solving for $k_{obs}$.

$$k_{obs}(T) = \frac{1 - m(T)}{t} \quad [2]$$

In Eq. 2, temperature (T) is the variable of interest when using the PTIR method, as t is held constant for a given experiment. The PTIR analysis method is valid for initial-rate conditions, where the rate of degradation remains approximately constant. This is also expected to hold for other degradation processes (e.g., chemical degradation with breaking of covalent bonds) not investigated here, as the principle of initial rates in reaction kinetics is more general than just the example shown here.

Differential Scanning Calorimetry (DSC) to Guide the Choice of Incubation Temperatures If one has preliminary data to indicate the rate of aggregation at one temperature, the following is unnecessary. But if one is starting with no knowledge of aggregation rates for the protein and solution conditions of interest, the following way is useful for determining a starting point for PTIR in terms of guiding which temperature range to use for measuring aggregation rates.

Figure 2:
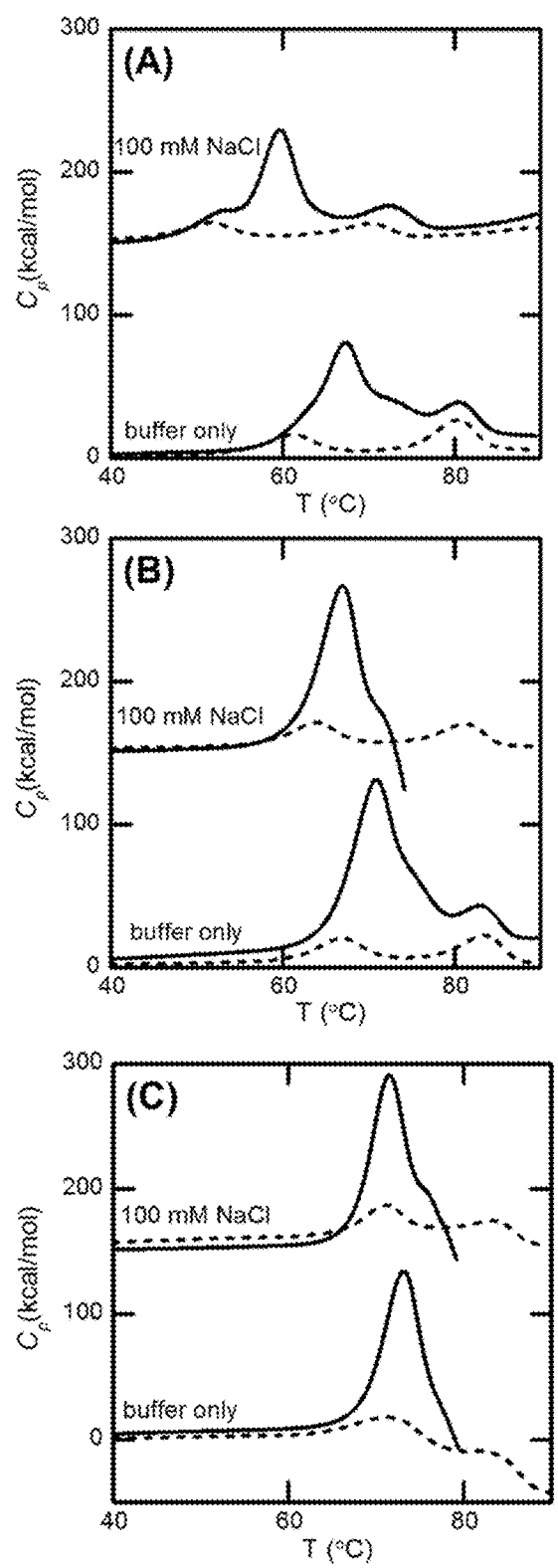
FIG. 2 shows DSC traces for IgG1 (solid) and Fc-IgG1 (dashed) formulated in 10 mM acetate buffer at pH 4 (A), pH 5(B), and pH 6 (C) with no added salt or with 100 mM NaCl added salt (offset 150 kcal/mol). Curves are offset vertically for easier visualization.

FIG. 2 shows thermograms for AS-IgG1 (solid) and the corresponding Fc fragment (dashed) at pH 4 (panel A), pH 5 (panel B), and pH 6 (panel C) in 10 mM acetate. Previous work reported DSC thermograms for AS-IgG1 at the same pH and NaCl concentrations, but in 5 mM citrate buffer. In FIG. 2, profiles for conditions with 100 mM added NaCl are offset vertically to distinguish them from those with no added NaCl. The peaks of the Fc-IgG1 thermograms overlay with the smaller peaks or shoulders of the full IgG1 thermogram in panels A to C. As expected based on previous literature reports, there are only two, relatively small, transitions for the Fc-IgG1 when compared with the full IgG1; the peak at lower (higher) temperature is assigned to the $C_H 2$ ($C_H 3$) domain of the Fc. For the full IgG1, the peak for the Fab domains overlaps with one or both peaks from the Fc domains, depending on the solution pH. The DSC profiles are consistent with the pH dependent thermograms reported in the literature for a range of other IgG1 molecules as a function of pH and salt concentration. Prior work by Kim et al. showed that aggregation involved unfolding of the Fab domain for this IgG1.

Aggregation Rates from PTIR Versus Standard Isothermal Approaches

The DSC thermograms were used to guide the initial choices for incubation temperatures for accelerated aggregation rates. All incubation temperatures were selected to be below the DSC Fab peak temperatures for a given solution condition, based on the discussion above. Aggregation rates were determined using the PTIR method and quantitatively compared to those determined by canonical isothermal-rate experiments. Aggregation rates or initial-rate coefficient ($k_{obs}$) values were calculated based on Eq. 1 or 2 above. Using a single sample at each temperature for the PTIR approach provides a "worst case" example, as one could easily use more than one incubation time or replicate samples at a given incubation time for each temperature. However, the results below indicate that this may not be necessary if one has sufficiently high-precision results with the assay of choice (e.g., SEC in the present case).

Figure 3:
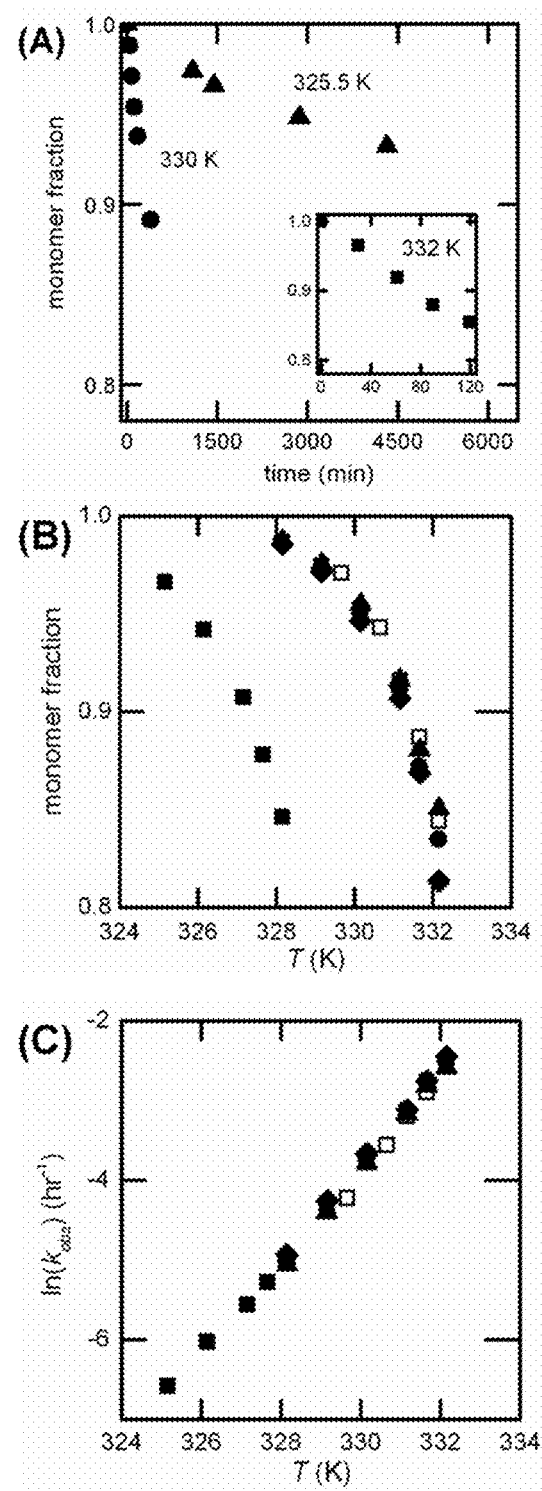
FIG. 3 shows exemplary isothermal and PTIR results for determining IgG1 aggregation rates at pH 5, (5 mM citrate buffer), and in the same buffer but with the addition of 100 mM NaCl. (A) Isothermal monomer loss versus time at 325.5° K (triangles), 330° K (circles), and 332° K (squares shown in the inset). (B) PTIR monomer loss at 2 hours (triangles, circles, diamonds, and open squares) or 24 hours (closed squares) as a function of incubation temperature. (C) Calculated $\ln(k_{obs})$ values derived from PTIR data.

FIG. 3 compares the results obtained by standard isothermal monomer loss kinetics (panel A) with those obtained by the PTIR method (panel B), using 1 mg/mL IgG1 in pH 5 buffer (5 mM citrate) with 100 mM added NaCl. Panel A shows isothermal monomer loss as a function of incubation time (t) for 325.5° K (triangles), 330° K (circles), and 332° K (squares shown in the inset). Visual inspection of FIG. 3, panel A reveals that monomer loss was linear versus t over the experimental range tested (m=1-0.8). Previously reported work also showed linear kinetics during initial periods of aggregation, which is expected based on general mass action kinetic considerations when the extent of reactant consumption is small. When operating in the initial-rate regime, one does not need to know or assume the reaction mechanism. However, if one operates at much larger extents of monomer loss (m<<1), the monomer loss profile is expected to become non-linear, and this requires one to determine or assume the underlying aggregation mechanism to accurately quantify the net or observed rate coefficient for monomer loss ($k_{obs}$).

FIG. 3 panel B shows aggregation rates determined by using the PTIR method according to the invention. The symbols show m as a function of incubation temperature for 2-hour (circles, diamonds, triangles and open squares) and 24-hour (closed squares) incubation times. Different temperatures were used for the 2-hour and for the 24-hour experiments, based on the discussions above and below. For the 2-hour experiments, three separate protein stocks were prepared and the experiment was repeated on separate days to provide a simple assessment of variability. Scatter in the data in FIG. 3 panels B and C shows typical experimental uncertainty expected with the PTIR approach. The value of m for each symbol in FIG. 3 panel B was converted to $k_{obs}$ using Eq. 2, with the corresponding values of $\ln(k_{obs})$ being given in FIG. 3 panel C. The symbols in panel C correspond to those in panel B for a given solution condition, for a given set of temperature values. Error bars are smaller than the size of the symbols unless visible in either panel.

As the PTIR approach is valid in the initial rate regime (m=1 to approx. 0.8), aggregation rates measured at longer times necessarily correspond to incubations at lower temperature(s). The 24-hour time-scale experiments were chosen to extend the range of accessible $k_{obs}$ values by at least an order of magnitude. Ten-day incubations were also performed (data not shown in FIG. 3), but in many cases significant fragmentation occurred, and this convolutes the interpretation and analysis to properly determine monomer loss rates for monoclonal antibodies. No data are reported here, or were used in subsequent analysis, for which fragmentation was evidenced in SEC.

The results in FIG. 3 illustrate that one obtains temperature-dependent rates of aggregation for many temperatures (e.g., 15 values in FIG. 3 panel B) with the PTIR method, while using the same amount of protein material as was required to obtain rates for only three temperatures via standard methods (i.e., FIG. 3 panel A). The overlapping data sets in FIG. 3 panel B are from repeat experiments using freshly prepared protein stock solutions on separate days, to illustrate that the PTIR results are robust and reproducible. This example illustrates the PTIR method, its reproducibility, and its comparable material needs to standard methods for determining rates at a single or small set of temperatures.

Figure 4:
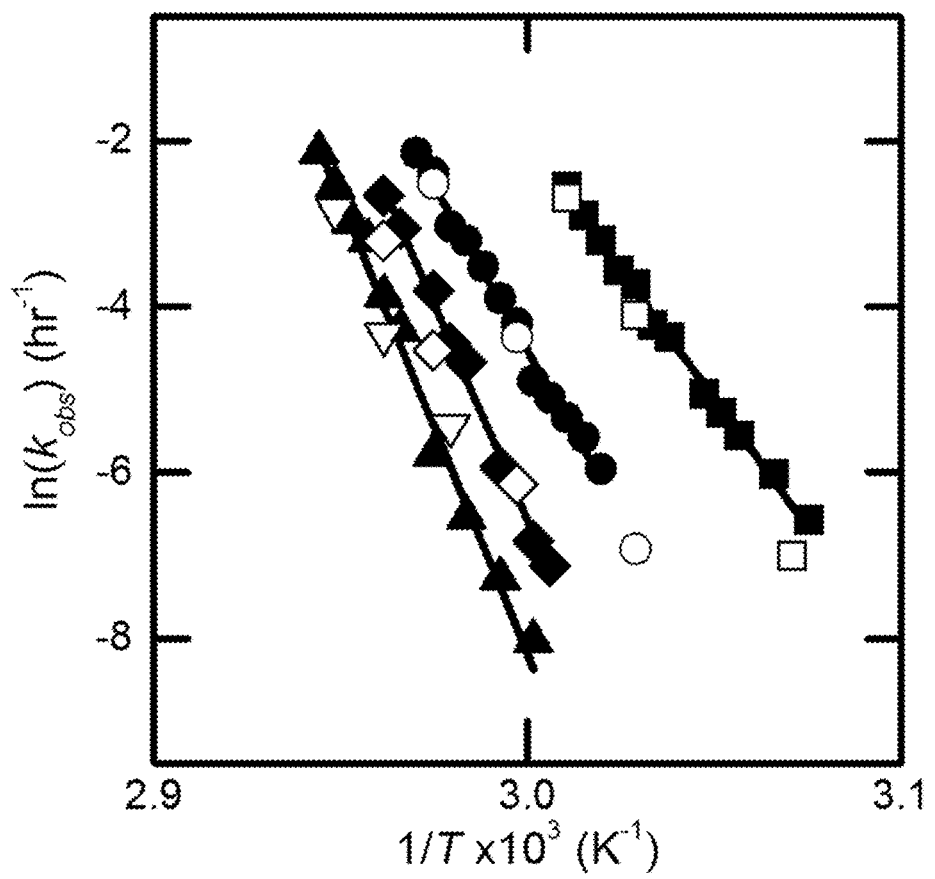
FIG. 4 shows an Arrhenius plot of the natural logarithm of the aggregation rate, or equivalently $\ln(k_{obs})$ as a function of inverse temperature, derived from PTIR data and showing comparison to results from traditional isothermal experiments. Closed symbols are from the PTIR data, and open symbols are from the traditional method. Different data sets are for different solution conditions, summarized below.

The examples below show that the PTIR method provides accurate rate values when compared to the standard method for a single temperature, and superior results when considering the temperature-dependence of aggregation rates.
Comparison of PTIR and Isothermal Incubations FIG. 3 illustrates the standard method (panel A) and the PTIR method (panel B) for a single solution condition. FIG. 4 summarizes results analogous to those in FIG. 3 for AS-IgG1 for a range of solution conditions, and also compares the rates determined from PTIR (across a range of temperatures) with those from the standard method applied at particular temperatures. The results in FIG. 4 compare the values of the logarithm of $k_{obs}$ versus inverse temperature (i.e., an Arrhenius diagram) for the different methods, demonstrating that the PTIR approach allows one to efficiently and accurately measure temperature-dependent aggregation rates across a range of temperatures. Each data set corresponds to a different solution condition with 5 mM sodium citrate buffer: pH 5, no added NaCl (diamonds); pH 5, 100 mM added NaCl (triangles); pH 6, no added NaCl (squares); and pH 6, 100 mM added NaCl (closed circles). The open symbols in FIG. 4 show the $k_{obs}$ values determined from traditional isothermal incubation (i.e., analogous to the data in FIG. 3 panel A), while closed symbols are for the PTIR method (i.e., analogous to the data in FIG. 3 panel B). The conditions for FIG. 3, panels A and B are the same as those for the closed diamonds in FIG. 4.

The aggregation rates determined via the PTIR approach are comparable in accuracy to those obtained by the standard isothermal aggregation method, which uses many samples at the same temperature, while the PTIR method provides rates for many more temperatures, using comparable consumption of protein material and user time. As noted above, the results provided here are a "worst case" example for accuracy using PTIR, in that only a single incubation time was used for a given temperature in the PTIR method.
Determination of Activation Energies An important use for values of $k_{obs}$ vs. T is to determine an accurate value of the effective activation energy ($E_a$) of aggregation, so that accelerated aggregation rates may be more effectively extrapolated to lower temperatures—e.g., for predicting room temperature shelf life. Intuitively, having $k_{obs}$ values at more T values will allow one to regress $E_a$ values with much better statistical confidence intervals and will provide greater ability to extrapolate $k_{obs}$ to lower temperatures.

FIG. 4 shows an Arrhenius diagram of aggregation rates determined using the PTIR device and traditional isothermal incubations. The results show so-called Arrhenius behavior, in that the data are effectively linear when plotted as ln $k_{obs}$ vs. 1/T. Based on FIG. 3, it is apparent that if one uses comparable amounts of material for both PTIR and traditional isothermal experiments, PTIR provides almost an order of magnitude increase in the number of temperatures that can be tested. This increased information regarding the temperature dependence of the rates provides for much more reliable $E_a$ values, as illustrated below.

The data were regressed using the Arrhenius equation (Eq. 3), where $k_{obs}$ is the experimentally determined value for reaction rate coefficient (units of inverse time), $E_a$ is defined above, $k_0$ is the value of $k_{obs}$ at an arbitrarily chosen temperature, $T_0$. In each case below, $k_0$ was a fitting parameter and $T_0$ was selected as 333.15° K because that is near the median of all incubations temperatures. Choosing different values for $T_0$ shifted the fitted value and confidence interval for $k_0$, but not for $E_a$. Values of T are in ° K.

$$k_{obs} = k_0 \exp\left(\frac{E_a}{R}\left(\frac{1}{T} - \frac{1}{T_0}\right)\right) \quad [3]$$

Table 1 reports the pre-factors ($k_0$) and activation energies ($E_a$) from Arrhenius fits using data plotted in FIG. 4 for PTIR and canonical isothermal incubations. Three temperatures were used for the canonical method (see open symbols in FIG. 4). Notably, current guidelines from regulatory agencies for accelerated stability tests for pharmaceutical products require even fewer than three incubation temperatures.

TABLE 1

|  | PTIR Method | | Canonical Isothermal Method | |
| --- | --- | --- | --- | --- |
|  | $k_0$ (hr$^{-1}$) | $E_a$ (kcal/mol) | $k_0$ (hr$^{-1}$) | $E_a$ (kcal/mol) |
| pH 5 0 mM NaCl | (9.5 ± 0.9) × 10$^{-3}$ | 156 ± 12 | (7 ± 20) × 10$^{-3}$ | 200 ± 300 |
| pH 5 100 mM NaCl | 0.122 ± 0.015 | 123 ± 6 | 0.12 ± 0.12 | 140 ± 50 |
| pH 6 0 mM NaCl | (2.3 ± 0.8) × 10$^{-4}$ | 220 ± 20 | (0.5 ± 5) × 10$^{-3}$ | 200 ± 400 |
| pH 6 100 mM NaCl | (1.2 ± 0.2) × 10$^{-3}$ | 206 ± 15 | (1.4 ± 3.8) × 10$^{-3}$ | 200 ± 200 |

Visual inspection of Table 1 shows the PTIR approach results in much smaller confidence intervals for fitted parameters. In contrast, the confidence intervals on the parameters regressed for the standard isotherm experiments are so large that the fitted parameters are statistically meaningless (e.g., the uncertainty in $E_a$ is as large as the value of $E_a$ itself). These results further illustrate the effectiveness of using the PTIR method and device to determine temperature-dependent aggregation rates, as well as illustrating greatly improved determination of activation energies if one chooses to regress rate data using the Arrhenius equation.
Shelf-Life Prediction and Non-Arrhenius Rates Although not shown herein, the PTIR approach can be extended to longer incubation times (multiple days to months) to yield results that may be predictive of rates at even lower temperatures (e.g., refrigerated or room-temperature conditions). This would be straightforward for any degradation route for which Eq. 3 is an accurate description. For example, deamidation and, more generally, hydrolysis reactions in aqueous solution, are typically Arrhenius over the relevant temperature range for pharmaceutical products.

In the present case, aggregation rates were measured over relatively small temperature windows (i.e., net change in rates on the order of 10$^2$), and therefore an Arrhenius equation is expected to be valid. If one does not need to extrapolate more than approximately one order of magnitude (e.g., a factor of 10-20, or from 1 month to almost 2 years), it is reasonable to expect that the Arrhenius equation will hold reasonably well for such an extrapolation if the data under accelerated conditions show Arrhenius behavior (Roberts et al. *Int. J. Pharm.* 48:318-333 (2011)). As the desired shelf life for typical pharmaceutical products is at least 18 months, and usually is targeted for 18-24 month, the present invention can greatly improve the ability of workers to make reliable predictions of product shelf life.

Alternatively, it has been reported that, when considering rates over a much broader range of time scales (i.e., many orders of magnitude), non-Arrhenius behavior may become significant for protein aggregation. The term non-Arrhenius in this context refers to cases where the activation energy depends on temperature (i.e., data are curved or show a "kink" or breakpoint in a diagram of the type shown in FIG. 4). In this case, one is advised to not rely on Eq. 3, or its analogous mathematical forms, for use with the entire temperature range. Rather, one should either regress $k_{obs}$ vs. temperature to a non-Arrhenius model if one has confidence that model is appropriate, or one should use only the PTIR data from the temperatures closest to those of interest for shelf life predictions. That is, rather than regress a model such as the Arrhenius model to data spanning many orders of magnitude for $k_{obs}$, one instead focuses on determining the "local" activation energy based on the $k_{obs}$ data that span one to two orders of magnitude and lie at the temperatures closest to those of interest for shelf life predictions. The idea of using a local $E_a$ values is equivalent to using the local slope, or tangent, to a curve in numerical integration. Such an idea was suggested by one of the inventors previously (Wang and Roberts, *AAPS J*. (online only) doi: 10.1208/s12248-013-9485-3 (2013)), but this approach requires accurate rate data for many temperatures. As such, the PTIR method enables shelf life prediction in such non-Arrhenius situations.

Discriminating Effects of pH, Buffer Type, and NaCl on Aggregation Rates and $E_a$ Values Knowledge of activation energies is important for extrapolating rates and predicting shelf lives, but also has value for improved understanding of the underlying degradation rates, as this may influence decisions regarding which conditions will be optimal for a given product. The present example extended the case above for aggregation of AS-IgG1 to compare the buffer type (acetate vs. citrate) for the same pH and NaCl ranges used above.

Figure 5:
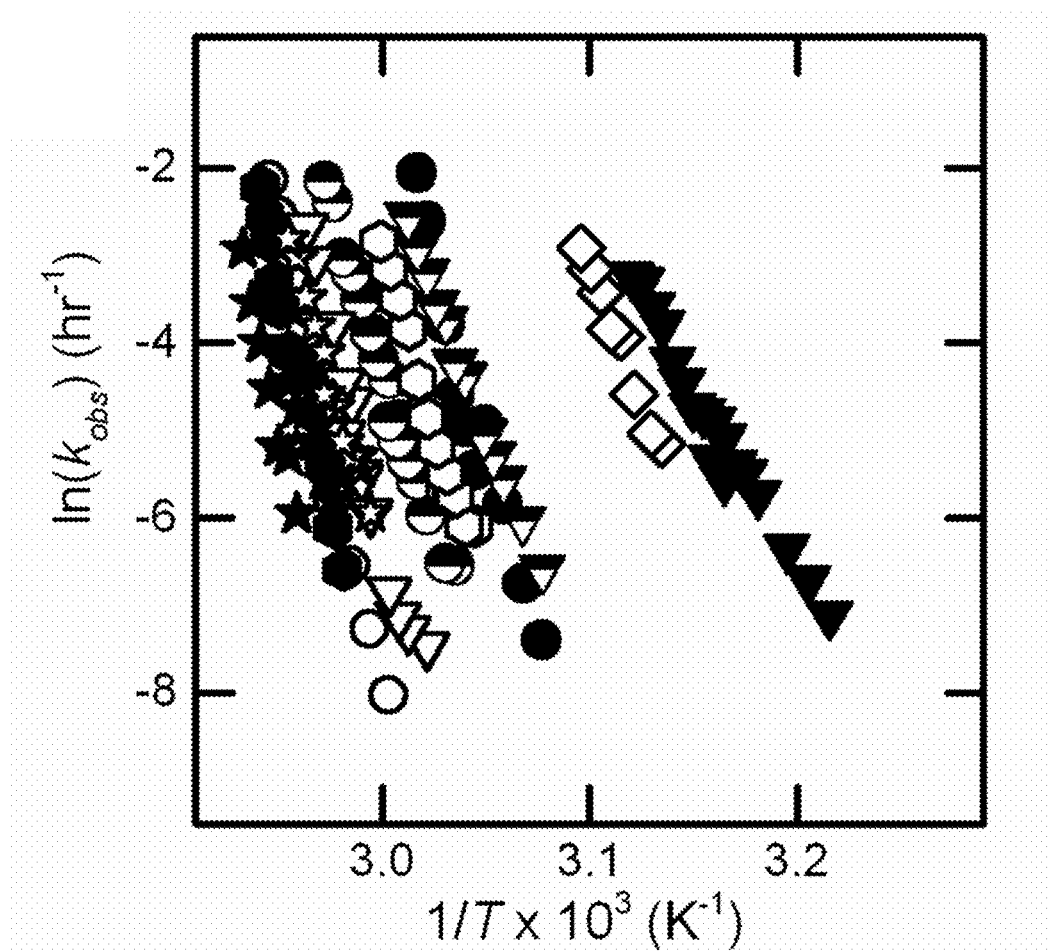
FIG. 5 shows an Arrhenius plot using PTIR data for 2 hour and 24 hour incubations across a broader range of solution conditions when compared to FIG. 4.

Values of $k_{obs}(T)$ were determined as a function of pH (4, 5, 6), added NaCl concentration (0 mM or 100 mM), and buffer species (citrate or acetate). FIG. 5 is an Arrhenius diagram based on the PTIR method for all solution conditions that were tested, including 2 hour and 24 hour incubations. Symbols shown in FIG. 5 are as follows.

| Shape | pH | mM NaCl | Buffer |
| --- | --- | --- | --- |
| Triangle, open | 6 | 100 | 5 mM citrate |
| Triangle, closed | 4 | 100 | 5 mM citrate |
| Triangle, split | 5 | 100 | 5 mM citrate |
| Circle, open | 6 | 0 | 5 mM citrate |
| Circle, closed | 4 | 0 | 5 mM citrate |
| Circle, split | 5 | 0 | 5 mM citrate |
| Hexagon, open | 5 | 100 | 10 mM acetate |
| Hexagon, closed | 5 | 0 | 10 mM acetate |
| Star, open | 6 | 100 | 10 mM acetate |
| Star, closed | 6 | 0 | 10 mM acetate |
| Diamond, open | 4 | 100 | 10 mM acetate |

Previously reported work qualitatively showed that changing buffer species could significantly alter aggregation rates. Additionally, the results above indicate that IgG1 formulated at pH 4 in 10 mM acetate buffer with no added salt resulted in no aggregation (monomer loss data not shown) even after heating at 85° C. for one hour.

From visual inspection of FIG. 5, it is clear that no single incubation temperature would be practical to achieve aggregation rates on a comparable timescale (hours to weeks) for all solution conditions. For example, if one selected a temperature to achieve a rate corresponding to $\ln(k_{obs})=-7$ for solution conditions indicated with the closed circles, the rates for solution conditions depicted with closed triangles would be so large as to be impractical to measure (and vertically far off-scale in FIG. 5). This highlights another utility of the PTIR approach, i.e., that it allows one to obtain $k_{obs}(T)$ profiles for head-to-head comparison between solution conditions or different proteins that would otherwise be untenable to quantitatively compare if one had to select a common temperature for measuring aggregation rates.

Figure 6:
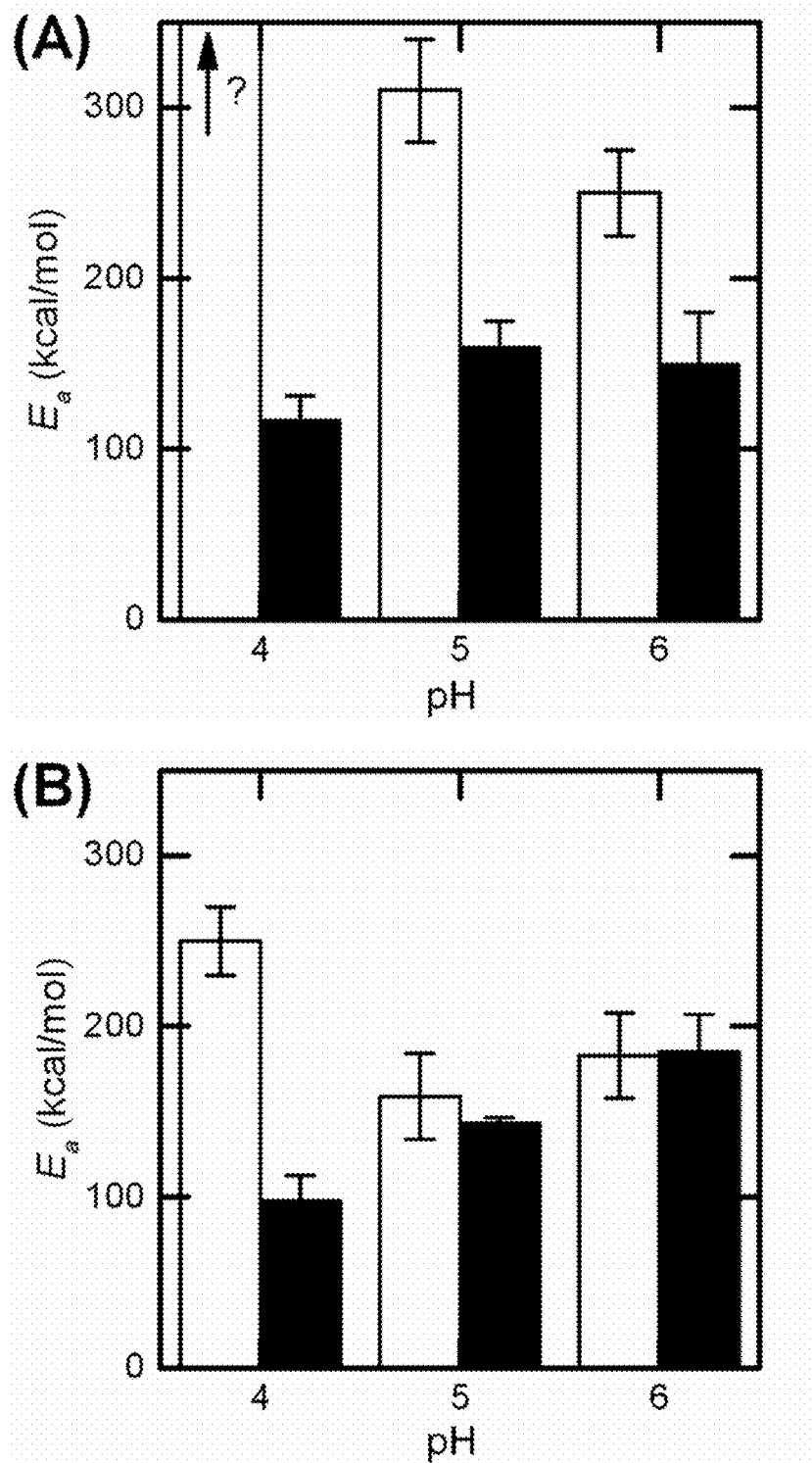
FIG. 6 shows effective aggregation activation energies for IgG1, determined from PTIR data as a function of pH and with or without 100 mM added NaCl. (A) 10 mM acetate (B) 5 mM citrate.

FIG. 6 shows $E_a$ values and 95% confidence intervals determined from fitting 2-hr PTIR data to Eq. 3 for each of the formulation conditions in FIG. 5, with the panels A and B for those formulations prepared in 10 mM acetate buffer, and 5 mM citrate buffer, respectively. For each pH, formulations prepared without added NaCl are shown as open bars and those with 100 mM NaCl concentration are shown as closed bars. Notably, pH 4 with no added NaCl and 10 mM acetate had an unmeasurably large $E_a$ value, as IgG1 heated in this formulation did not aggregate. The question mark in the open bar at pH 4 in FIG. 6 (panel A) indicates that $E_a$ is unknown for that condition because aggregation was too slow to measure.

At 100 mM added NaCl, $E_a$ increases with increasing pH, which is expected as conformational stability (i.e., $T_m^{app}$) increases with pH. Based on previously reported thermodynamic arguments and qualitative mechanistic arguments for non-native aggregation, larger $T_m^{app}$ values imply increased unfolding enthalpy values, and therefore higher $E_a$ values. However, $E_a$ values at low ionic strength conditions (no added NaCl) for acetate buffer show the opposite behavior. That is, $T_m^{app}$ values decrease as one decreases pH, but $E_a$ values increase substantially.

The present results highlight that both conformational stability and inter-protein interactions can play a discernable role in determining aggregation rates (monomer loss). Although the canonical isothermal method was not employed in this example, the results in Table 1 and FIG. 4 illustrate that one can expect error bars or uncertainties in $E_a$ values from traditional methods that are almost a factor of 10, or larger, compared to those from the PTIR method when using comparable amounts of material. If one were to increase the error bars to that extent in FIG. 6, the important trends and differences would not be discernable within statistical uncertainty. As such, PTIR provides a means to determine more accurate and reliable activation energies that can be enabling for a variety of applications, including more rational and accurate selection of optimal product formulation conditions.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of determining the reaction rate coefficient ($k_{obs}$) for the degradation of a chemical species at each of a plurality of constant temperatures, comprising in sequence the steps of
   a) simultaneously incubating a plurality of samples of the chemical species in a single unitary device at said plurality of constant temperatures T, wherein the incubation of each of the plurality of samples is performed for an incubation time t selected to result in loss of a portion of the chemical species, said portion being at most 20 mol % of the amount originally present, where the choice of t might or might not be the same for each value of T;

b) quenching each of the samples in a manner sufficient to stop degradation;

c) determining the mole fraction m of the chemical species remaining in each of the quenched samples, relative to the amount present before incubating; and d) determining for each sample a reaction rate coefficient $k_{obs}$ according to the equation $$k_{obs}(T) = \frac{1 - m(T)}{t}.$$

2. The method of claim 1, wherein the chemical species is a pharmaceutical product.

3. The method of claim 1, wherein the chemical species is a protein.

4. The method of claim 3, wherein the degradation comprises aggregation.

5. The method of claim 3, wherein the degradation comprises non-native aggregation.

6. The method of claim 3, wherein the degradation comprises chemical degradation.

7. The method of claim 1, wherein the loss of the chemical species is at most 10 mol %.

8. The method of claim 1, further comprising e) performing numerical regression of the $k_{obs}$ values obtained in step d) and the corresponding temperatures T in ° K to derive the activation energy $E_a$ of the degradation of the chemical species according to the following equation $$k_{obs} = k_0 \exp\left(\frac{E_a}{R}\left(\frac{1}{T} - \frac{1}{T_0}\right)\right)$$

wherein $k_0$ is the value of $k_{obs}$ for $T_0$, one of the plurality of temperatures in ° K.

9. The method of claim 8, wherein the chemical species is a pharmaceutical product.

10. The method of claim 8, wherein the chemical species is a protein.

11. The method of claim 10, wherein the degradation comprises aggregation.

12. The method of claim 10, wherein the degradation comprises non-native aggregation.

13. The method of claim 10, wherein the degradation comprises chemical degradation.

14. The method of claim 8, wherein the loss of the chemical species is at most 10 mol %.

* * * * *